United States Patent [19]

Ocheltree et al.

[11] Patent Number: 5,084,588
[45] Date of Patent: Jan. 28, 1992

[54] REDUCING HALIDE CONTAMINATION IN ALKOXY SILANES

[75] Inventors: Robert L. Ocheltree, Pennsboro, W. Va.; James S. Ritscher; Scot M. Turner, both of Marietta, Ohio; Renate I. Warren, Coolville, Ohio

[73] Assignee: Union Carbide Chemicals & Plastics Technology Corporation, Danbury, Conn.

[21] Appl. No.: 605,344

[22] Filed: Oct. 30, 1990

Related U.S. Application Data

[63] Continuation of Ser. No. 548,596, Jul. 5, 1990, abandoned.

[51] Int. Cl.$^5$ ............................ C07F 7/18; C07F 7/20
[52] U.S. Cl. ................................................ 556/466
[58] Field of Search ........................................ 556/466

[56] References Cited

U.S. PATENT DOCUMENTS

| | | | |
|---|---|---|---|
| 4,281,146 | 7/1981 | Ashby | 556/456 |
| 4,827,008 | 5/1989 | Gousetis et al. | 556/466 |
| 4,851,558 | 11/1989 | Nishida et al. | 556/471 |
| 4,861,907 | 8/1989 | Wright et al. | 556/419 |
| 4,956,486 | 9/1990 | Marko et al. | 556/466 |
| 4,962,221 | 10/1990 | Huntress et al. | 556/466 X |

*Primary Examiner*—Paul F. Shaver
*Attorney, Agent, or Firm*—Bonnie L. Deppenbrook

[57] ABSTRACT

A method for reducing the level of acidic halide contamination in alkoxy silanes, particularly amino alkoxy silanes, by contacting said silane with a salt of an acid having a dissociation constant of greater than about $10^{-15}$.

20 Claims, No Drawings

REDUCING HALIDE CONTAMINATION IN ALKOXY SILANES

This application is a continuation of prior U.S. application Ser. No. 548,596, filed July 5, 1990, now abandoned.

BACKGROUND OF THE INVENTION

1. Field of the Invention

The present invention is directed to a process for reducing the level of acidic halide contamination in alkoxy silanes, particularly the level of chloride contamination in amino alkoxy silanes.

2. Description of Related Art

Siyl esters, also referred to as silyl ethers, i.e., organic silanes having alkoxy or aryloxy substituents, are typically prepared by reacting an organic silyl halide (halosilane) with an alcohol or phenol sometimes in the presence of an acidic acceptor to neutralize by-product acidic halide. Amino alkoxy silanes are conveniently prepared by reacting an alkoxy alkyl silyl halide having the formula $(RO)_n R'_{3-n} SiR''X$ where X is a halide and n is a number between 1 and 3, with a primary amine $(R'''NH_2)$ or a secondary amine $(R''''_2NH)$. R, R', R'', R''' and R'''' can be any of a wide variety of organic radicals including saturated or unsaturated aliphatic hydrocarbon radicals or aromatic radicals. Again, an acidic halide is produced as a by-product of the reaction.

In such systems, halide (e.g., chloride) contamination from by-product acidic halide is a reoccurring problem, particularly when the product is an aminosilane because a portion of the by-product acid, generally hydrogen chloride, unavoidably is neutralized by the amino moiety of the resulting aminosilane. This halide contamination of the silane product is undesired for a variety of reasons, including the potential for corrosion.

In the past, acidic halide contamination of alkoxy silanes generally, and particularly amino-substituted silanes, has been controlled by a post-reaction treatment with a strong base such as a metal alkoxide, e.g., sodium methoxide. Many of the commonly-used inorganic alkaline neutralizing agents, such as the alkali metal hydroxides, cannot be used, particularly in the case of alkoxy silanes, because water is produced by the neutralization reaction and contributes to silane product degradation via a hydrolysis mechanism. The same is true for sodium bicarbonate, which has been used for neutralizing certain organosilanes in the past. By-product water is a particularly troubling problem for higher molecular weight alkoxy silanes as it can lead to silane gelation.

Unfortunately, the quality of the silane product can also be adversely affected by the level of metal alkoxide addition. If an insufficient amount of the metal alkoxide is added, an undesirably high residual halide level is encountered in the silane product. On the other hand, the addition of even a small excess of the metal alkoxide commonly causes an unacceptably severe and irreversible color development in the alkoxy silane product, particularly those products having amine substitution. Such coloration is thought to be due to oxidation of the amine in the presence of the excess base.

Alkoxy silanes and amino-substituted alkoxy silanes in particular, find use in a variety of applications such as in laundry additives, and in caulking formulations, and as coupling agents between inorganic and organic surfaces such as a coupling agent for glass fiber. Normally these silane products have a very pale coloration. Thus, strong product coloration can be a significant problem confronting such uses.

In light of the above, great care must be exercised to obtain a proper neutralization end point when metal alkoxides are used for halide removal. This degree of care is very inconvenient and problematic in an industrial context. Use of metal alkoxy neutralization, therefore, tends to be very time-consuming and often leads to the unecomonical reworking, e.g., distillation, or in the extreme, discarding of over-neutralized products.

The present invention is directed to a new procedure for neutralizing alkoxy silanes, and amino-functional alkoxy silanes in particular, which essentially avoids the color-forming reactions encountered in the prior art procedure.

DESCRIPTION OF THE INVENTION

The present invention is directed to a method for reducing the quantity of acidic halide in an alkoxy silane, particularly in amino alkoxy silanes, which avoids oxidative degradation of the silane. Such oxidative degradation may contribute to unacceptable color formation in the silane.

According to the invention, the alkoxy silane containing the acidic halide contaminant is contacted with an alkali metal or alkaline earth metal salt of an acid, which salt does not form water as a by-product upon accepting a proton during the neutralization reaction. Preferably, the silane is contacted with a molar excess of the salt relative to the quantity of acidic halide in the alkoxy silane. Generally, a 100 to 200% molar excess should be sufficient. Suitable acids from which the salts used in the present invention originate are those having a dissociation constant ($K_a$) of greater than about $10^{-15}$. Preferably, the acid from which the salt originates has a dissociation constant between about $10^{-12}$ to $10^{-2}$ and most preferably the salt originates from a weak acid having a dissociation constant between about $10^{-9}$ and $10^{-4}$. The dissociation constant of the acid is determined in aqueous solution using procedures well known to those skilled in the art. Tabulated values for dissociation constants of commonly encountered acids are available from numerous sources, see, for example Masteron and Slowinski, *Chemical Principals*, 4th ed., (1977), p.460 and Hendrickson et. al., *Organic Chemistry*, 3rd ed., (1970), pp. 132, and 304–307.

In a particularly advantageous embodiment of this process, the halide-contaminated alkoxy silane first is treated with a metal alkoxide in less than a molar equivalent amount relative to the quantity of acidic halide in the silane. This alternative embodiment takes advantage of the stronger alkaline character of the metal alkoxide to neutralize a major portion of the acidic halide prior to treatment with the alkali metal or alkaline earth metal salt.

While the present invention is useful for removing or reducing the level of acidic halide contamination in a wide variety of alkoxy silanes, it is particularly useful for treating amino alkoxy silanes. Exemplary silanes include vinyltrimethoxysilane, vinyltriethoxysilane, chloropropyltrimethoxysilane, octyltriethoxysilane, N-(β-aminoethyl)-γ-aminopropyltrimethoxysilane, N-[(β-aminoethyl)-N'-β-aminoethyl)-γ-aminopropyltrimethoxysilane, N,N-bis(trimethoxysilylpropyl)amine, N-phenyl-γ-aminopropyl trimethoxy silane, N,N-diethyl-γ-aminopropyltrimethoxysilane and the like.

Suitable acids from which originate the alkali metal or alkaline earth metal salts useful in the present invention, hereinafter alternatively referred to as "basic salts", include acetic acid, benzoic acid, propionic acid, phosphoric acid, sulfuric acid, sulfurious acid, formic acid, butyric acid, boric acid, succinic acid, glutaric acid, adipic acid, and the like. One should not use acids that can cause undesirable side reactions in the silane, such as polymerization reactions which might be encountered using $\alpha,\beta$ unsaturated acids. Suitable basic salts include such materials as sodium acetate, sodium benzoate, sodium propionate, disodium hydrogen phosphate, sodium sulfite, trisodium phosphate, sodium butyrate, sodium valerate, sodium polyacrylate, sodium formate, sodium succinate and disodium succinate, sodium gluterate and disodium gluterate, sodium adipate and disodium adipate, disodium tartarate, sodium metaborate, sodium othoborate, sodium sulfate, as well as the corresponding lithium, potassium and rubidium salts and the magnesium, calcium, strontium and barium salts. These salts all originate directly from a conjugate acid having a dissociation constant ($K_a$) of greater than about $10^{-15}$.

Particularly preferred basic salts are the alkali metal and alkaline earth metal acetates and propionates. Sodium acetate and sodium propionate are particularly preferred.

To be suitable in the present invention, the basic salt must be used in its anhydrous form and neutralization of the acidic chloride the silane by the basic salt must not produce by-product water. In other words, the contacting of the alkoxy silane with the basic salt should be done under substantially anhydrous conditions.

Treatment of the alkoxy silane may be accomplished simply by adding the basic salt to the silane with sufficient agitation to insure intimate contact between residual acidic halide and salt. The salt can be added either in a solid, preferably granular, form or as a slurry in an organic solvent compatible with the silane. A polar organic solvent including alkanols such as methanol often may be useful. It may also be possible to conduct the neutralization by percolating the alkoxy silane through a fixed bed of the basic salt. In the broad practice of the present invention, any procedure for contacting the basic salt with the alkoxy silane can be used. Reaction between the basic salt and the acidic halide contaminant in the alkoxy silane produces, as neutralization products, the conjugate acid of the basic salt and the alkali metal or alkaline earth metal halide.

In order to prevent the acidic halide contamination from being simply replaced by another contaminant source as a consequence of the neutralization of the acidic halide, the basic salt must form either an insoluble acid or a volatile acid upon reaction with the acidic proton of the acidic halide, along with the insoluble alkali metal or alkaline earth metal halide salt. These products preferably are removed from the alkoxy silane, for example, as solids by filtration or by volatilation. Solids removal is best done using a simple filtration, although any solid/liquid separatory technique, including centrifugation and the like, can be used. Preferably, the silane is cooled prior to filtering to promote maximum precipitation (e.g., crystallization) of the solid neutralization products.

Basic salts which are only sparingly soluble in the alkoxy silane at a reduced temperature, such as at about ambient temperature, e.g. 25° C., but which exhibit greater solubility at higher temperatures are preferred.

As used herein, the phrase "sparingly soluble, is defined as a solubility of less than about one gram per 100 grams of the alkoxy silane, preferably less than about 0.5 gram per 100 grams, and most preferably less than about 0.1 gram per 100 grams. In this way, any residual excess of the basic salt is easily removed from the treated alkoxy silane as a solid, along with the neutralized acidic halide, by filtration.

The temperature at which the alkoxy silane and the basic salt are contacted is not narrowly critical. If the basic salt is added to the alkoxy silane as a solid, then contacting preferably is done at an elevated temperature of at least about 100° C. to facilitate maximum dissolution of the salt in the silane. Extreme temperatures that contribute to thermal degradation of the silane product, of course, must be avoided. If the basic salt is added to the silane as a slurry, such as in a polar solvent such as the (proper) alkanol, a lower treatment temperature may prove acceptable. The alkanol selected as a carrier solvent must not contribute to product degradation by an ester interchange with the alkoxy silane.

The silane and basic salt are contacted, e.g., by mixing, for a time sufficient to reduce the level of acidic halide contamination in the alkoxy silane. While the treatment time depends somewhat on treatment temperature, contacting, e.g., by mixing, normally should be continued for at least about two hours. Contacting times in excess of 24 hours should not be required.

It may also be necessary to remove other lower boiling contaminants from the treated, i.e., neutralized, alkoxy silane, such as methanol, which may be added or generated during the neutralization process. If the neutralization reaction produces a volatile acid by-product, that also may be removed at this time. Preferably this is done prior to the solid/liquid separation, e.g., filtration, of the halide salt by a vacuum assisted distillation or stripping step, such as by heating the alkoxy silane at a temperature of about 100° C. under a vacuum for a time sufficient to remove any low boiling contaminants. Although in the broad practice of the present invention, such treatment can be done after solids/liquid separation.

It has been found that the alkali metal or alkaline earth metal salts provide an adequate neutralization of acidic halide in alkoxy silanes but, presumably due to their buffering effect, over-neutralization of the silane is not a problem. Thus, over-neutralization does not make the alkoxy silane overly sensitive to oxidation and the accompanying color-forming reactions encountered when using metal alkoxides.

In a particularly useful embodiment, neutralization with the alkali metal or alkaline earth metal salt is done in cooperation with partial neutralization of the acidic halide contamination by a stronger base such as a metal alkoxide. Sodium methoxide is a particularly useful strong base. As with the basic salt, the strong base should not form water as a by-product of the neutralization reaction. The added base such as the metal alkoxide, should be limited to that amount needed to neutralize only up to about 80 to 90 mol percent of the acidic halide content of the alkoxy silane. In this way, over-neutralization and the accompanying oxidative degradation are avoided. The neutralization process is equally successful whether the metal alkoxide and basic salt are added simultaneously or whether the metal alkoxide is added first to the alkoxy silane followed by addition of the basic salt.

The present invention can be used to reduce the halide concentration of any alkoxy silane, but is especially useful for treating those alkoxy silanes which are highly susceptible to oxidative degradation in the presence of strongly basic materials. Thus, the present invention has particular utility for treating amino-functional alkoxy silanes which experience severe color changes as a consequence of such oxidative degradation.

The present invention will be described below in greater detail with reference to the examples, in which the parts and percentages are by weight unless otherwise indicated.

EXAMPLES

EXAMPLE 1

Crude N-$\beta$-aminoethyl-N'-$\beta$-aminoethyl-$\gamma$-aminopropyltrimethoxysilane containing acidic chloride was neutralized with less than a molar equivalent of sodium methoxide, relative to the quantity of acid chloride in the silane. The sodium methoxide was added as a 25% solution in methanol. After initial filtering, the treated silane contained about 0.28% soluble chloride measured as primary amine hydrochloride. Several 75.0 gram samples of the partially neutralized silane then were further treated with a molar excess, based on the amount of residual acid chloride, of three different alkali metal salts and were stirred continuously at ambient temperature for 17 hours. The residual soluble chloride of the treated silanes, after filtering, is shown in Table 1. Two chloride concentrations are reported for the filtered silane. The first entry in the Table is based upon silver nitrate titration of the silane. This measured value then was adjusted based on the measured sodium content of the silane, as determined by atomic absorption spectroscopy, and a second, adjusted value also is reported. The adjusted value accounts for the incomplete removal (filtering) of sodium chloride from the treated silane. Of these salts, the acetate showed the best ability in this test of removing the chloride contamination.

TABLE 1

| Salt | Salt Added (gms) | Chloride (ppm) | Sodium (ppm) | Adjusted Chloride (ppm) |
|---|---|---|---|---|
| Na$_3$PO$_4$ | 1.09 | 3110 | 321 | 2615 |
| Na$_2$HPO$_4$ | 1.42 | 3150 | 223 | 2806 |
| NaC$_2$H$_3$O$_2$ | 1.64 | 2000 | 735 | 867 |

EXAMPLE 2

The neutralization procedure of Example 1 was repeated except that the silane containing the added alkali metal salt was agitated for 2 to 3 hours at an elevated temperature. Table 2 reports the residual chloride concentration of the silane after initial treatment with sodium methoxide (Initial Cl) and after treatment with each basic salt (Final Cl). An adjusted chloride value for the fully treated silane also is reported. The use of an elevated temperature enhanced the degree of chloride removal.

TABLE 2

| Salt | Salt Added (gms) | Temp (°C.) | Initial Cl (ppm) | Final Cl (ppm) | Sodium (ppm) | Final Adjusted Cl (ppm) |
|---|---|---|---|---|---|---|
| Na$_3$PO$_4$ | 1.09 | 96 | 2615 | 1230 | 290 | 783 |
| Na$_2$HPO$_4$ | 1.42 | 100 | 2806 | 3100 | 223 | 2756 |

TABLE 2-continued

| Salt | Salt Added (gms) | Temp (°C.) | Initial Cl (ppm) | Final Cl (ppm) | Sodium (ppm) | Final Adjusted Cl (ppm) |
|---|---|---|---|---|---|---|
| NaC$_2$H$_3$O$_2$ | 1.64 | 99 | 867 | 1410 | 860 | 85 |

EXAMPLE 3

Example 1 was repeated on a larger scale by neutralizing 2616 grams of crude N'-$\beta$'-aminoethyl-$\gamma$-aminopropyltrimethoxysilane first with a solution containing 25% sodium methoxide and then with a molar excess, based on residual chloride, of anhydrous trisodium phosphate. The silane was treated with the acid salt for about 2–3 hours at 100° C. The final chloride concentration, as measured by silver nitrate titration, was 800 ppm, which when adjusted for residual sodium was reported as 693 ppm.

EXAMPLE 4

Fifty gram samples of the partially neutralized N'-$\beta$'-aminoethyl-$\beta$-aminoethyl-$\gamma$-aminopropyltrimethoxysilane of Example 1 were further treated with a potassium or calcium basic salt and were agitated for 3 hours at 100° C. Table 3 identifies the salts, their level of addition, and the resulting chloride concentrations, as determined by silver nitrate titration, of the treated silanes. As above, the measured chloride analysis also was adjusted for sodium, determined by atomic absorption spectroscopy, and an adjusted chloride value is reported.

TABLE 3

| Salt | Added Salt (gms) | Final Chloride (ppm) | Sodium (ppm) | Final Adjusted Chloride (ppm) |
|---|---|---|---|---|
| K$_2$HPO$_4$ | 1.16 | 2860 | 101 | 2704 |
| Ca$_{10}$(OH)$_2$(PO$_4$)$_6$ | 0.67 | 3060 | 171 | 2796 |

EXAMPLE 5

A variety of sodium, calcium, and potassium salts were used to treat 110 gram samples of N-$\beta$-aminoethyl-$\gamma$-aminopropyltrimethoxysilane containing 0.67% acid chloride contamination. The salt-silane mixtures were agitated for various times and at several temperatures, were filtered and were analyzed for chloride using silver nitrate titration. The results are reported in Table 4.

TABLE 4

| Salt | Added Salt (gms) | Contacting Time | Temp (°C.) | Final Chloride (ppm) |
|---|---|---|---|---|
| NaC$_2$H$_3$O$_2$ | 3.28 | " | R.T. | 2210 |
| Na$_2$HPO$_4$ | 3.0 | " | R.T. | 6080 |
| NaH$_2$PO$_4$ | 5.12 | " | R.T. | 6410 |
| NaC$_2$H$_3$O$_2$ | 1.64 | " | 65 | 750 |
| NaC$_2$H$_3$O$_2$ | 3.3 | " | 65 | 420 |
| Na$_2$HPO$_4$ | 3.0 | " | 65 | 6670 |
| NaH$_2$PO | 5.1 | " | 65 | 6370 |
| Na$_3$PO$_4$ | 2.3 | " | 65 | 3120 |
| Na$_2$SO$_3$ | 2.3 | " | 65 | 2860 |
| Ca$_{10}$(OH)$_2$(PO$_4$)$_6$ | 2.0 | 6 hrs | 65 | 6410 |
| K$_2$HPO$_4$ | 3.5 | " | 65 | 4010 |
| KH$_2$PO$_4$ | 5.5 | " | 65 | 5320 |

EXAMPLE 6

Several sodium salts were added in a molar excess to 110 gram samples of crude N-β-aminoethyl-γ-aminopropyltrimethoxysilane having a 0.603% chloride concentration. The salt-silane mixtures were agitated at 100° C. for one hour. The final chloride concentration is reported in Table 5.

TABLE 5

| Salt | Added Salt (gms) | Final Chloride (ppm) |
| --- | --- | --- |
| $(NaPO_4)_xNa_2O$ | 5.0 | 5340 |
| $NaC_2H_3O_2$ | 5.0 | 106 |
| NaCOOH | 5.0 | 106 |
| $Na_2S_2O_3$ | 5.0 | 2750 |

EXAMPLE 7

Five grams of sodium acetate were added to a 110 gram sample of N-β-aminoethyl-γ-aminopropyltrimethoxysilane having a 0.67% acidic chloride contamination. The salt-silane mixture was agitated for 1 hour at 100° C. After filtering, the silane had a residual chloride concentration as measured by silver nitrate titration, of 460 ppm.

EXAMPLE 8

Several 110 gram samples of N-β-aminoethyl-γ-aminopropyltrimethoxysilane, having an initial chloride concentration of about 0.6%, were treated with a combination of sodium acetate and methanol. The samples were heated for several hours at an elevated temperature. In one case, 0.5 grams of the methanol was used to "wet" the sodium acetate prior to adding it to the sample product, while in the other experiments the methanol and sodium acetate were added simultaneously, but separately, to the silane. The treated silane, after filtering, was analyzed for chloride using silver nitrate titration and for sodium by atomic absorption spectroscopy. The final chloride concentration reported in Table 6 is adjusted for the measured sodium content.

TABLE 6

| Salt | Added Salt (gms) | Added MeOH (gms) | Time (hrs) | Temp (°C.) | Adjusted Final Cl (ppm) |
| --- | --- | --- | --- | --- | --- |
| $NaC_2H_3O_2$ | 3.3 | 15.0 | 6 | 65 | 1110 |
| $NaC_2H_3O_2$ | 3.3 | 15.0 | 6 | 100 | 90 |
| $NaC_2H_3O_2$ | 5.0 | 15.0 | 6 | 100 | 40 |
| $NaC_2H_3O_2$ | 5.0 | 0.5 | 1 | 100 | 200 |
| $NaC_2H_3O_2$ | 5.0 | 0.0 | 1 | 100 | 460 |

EXAMPLE 9

Two hundred twenty gram samples of crude N-β-aminoethyl-γ-aminopropyltrimethoxysilane containing 0.603% acid chloride contamination were partially neutralized with sodium methoxide added as a 25% sodium methoxide in methanol solution followed by treatment with a molar excess of sodium acetate. The treated silane was vacuum distilled to remove methanol. After filtration, the neutralized silane was submitted for chloride and sodium analysis using silver nitrate titration and atomic absorption spectroscopy, respectively. An adjusted residual chloride level is reported in Table 7.

TABLE 7

| Added Salt (gms) | Added NaOMe Solution (gms) | Adjusted Chloride (ppm) |
| --- | --- | --- |
| 5.0 | 5.0 | 7 |
| 2.5 | 7.5 | 8 |

EXAMPLE 10

The process of Example 9 was repeated using a 2080 gram sample of the aminosilane. The silane was sequentially treated with 70 gms of the sodium methoxide solution and 20 grams of sodium acetate. After vacuum stripping and filtering the heated silane had an adjusted residual chloride content of 2 ppm.

EXAMPLE 11

Several 250 gram samples of crude N-β-aminoethyl-γ-aminopropyltrimethoxysilane having a 0.716% acid chloride concentration were partially neutralized with sodium methoxide (added as a 25% solution of sodium methoxide in methanol) and an excess of sodium acetate. The sodium methoxide and sodium acetate were added simultaneously to the silane. After vacuum stripping and filtering, the treated silane samples were analyzed for chloride and sodium content using silver nitrate titration and atomic absorption spectroscopy, respectively. The final chloride concentration is reported as an adjusted value in Table 8.

TABLE 8

| Added Salt (gms) | Added NaOMe Solution (gms) | Adjusted Chloride (ppm) |
| --- | --- | --- |
| 2.5 | 8.6 | 76 |
| 1.84 | 9.18 | 54 |
| 0.60 | 9.7 | 68 |
| 1.23 | 9.7 | 39 |
| 1.23 | 9.7 | 20 |
| 1.23 | 9.7 | 17 |
| 1.85 | 9.7 | 79 |
| 0.61 | 10.26 | 24 |

EXAMPLE 12

Example 11 was repeated except that instead of sodium acetate, barium and potassium acetate were evaluated. The potassium and barium acetates were added after the treatment with sodium methoxide rather than simultaneously as was done with the sodium salts. The residual chloride contamination after addition of the sodium methoxide was 0.068%. Results are reported in Table 9. As above, an adjusted chloride value is reported.

TABLE 9

| Salt | Added Salt (gms) | Adjusted Final Chlorine (ppm) |
| --- | --- | --- |
| $KC_2H_3O_2$ | 1.41 | 12 |
| $Ba(C_2H_3O_2)_2$ | 1.84 | 50 |

EXAMPLE 13

About a 250 gram sample of chloropropyltrimethoxysilane containing about 600 ppm of residual chloride was contacted for 3 hours at about 105° C. with 1.05 grams of sodium acetate. After cooling and filtering, the silane had a residual chloride concentration of about 20 ppm.

EXAMPLE 14

A sample of vinyltrimethoxysilane having a low chloride residual was mixed with vinyltrichlorosilane to increase its residual chloride content prior to neutralization. The resulting sample had a chloride content of 655 ppm. About 223 grams of the chloride contaminated sample was contacted for 3 hours at about 105° C. with 1.02 grams of sodium acetate. After cooling and filtering, the silane had a residual chloride concentration of about 27 ppm.

While certain specific embodiments of the present invention have been described with particularity herein, it will be recognized that various modifications thereof will occur to those skilled in the art and it is to be understood that such modifications and variations are to be included within the purview of this application and the spirit and scope of the appended claims.

We claim:

1. A method for reducing the quantity of acidic halide in an alkoxy silane comprising contacting said alkoxy silane under substantially anhydrous conditions with an alkali metal or alkaline earth metal salt of an acid, said acid having a dissociation constant ($K_a$) of greater than about $10^{-15}$.

2. The method of claim 1 wherein said alkoxy silane is contacted with a molar excess, relative to the quantity of said acidic halide in the alkoxy silane, of said alkali metal or alkaline earth metal salt of an acid.

3. The method of claim 2 wherein said dissociation constant is between about $10^{-12}$ and $10^{-2}$.

4. The method of claim 2 wherein said dissociation constant is between about $10^{-9}$ and $10^{-4}$.

5. The method of claim 3 wherein said acid is selected from the group consisting of acetic acid, benzoic acid, propionic acid, phosphoric acid, sulfuric acid, sulfurious acid, formic acid, butyric acid, boric acid, succinic acid, glutaric acid, and adipic acid.

6. The method of claim 5 wherein said acid is acetic acid or propionic acid.

7. A method for reducing the quantity of acidic halide in an alkoxy silane comprising initially contacting said silane with less than a molar equivalent amount, relative to the quantity of said acidic halide in said alkoxy silane, of an alkali metal or alkaline earth metal alkoxide and then contacting said alkoxy silane under substantially anhydrous conditions with an alkali metal or alkaline earth metal salt of a acid, said acid having a dissociation constant ($K_a$) of greater than about $10^{-15}$.

8. The method of claim 7 wherein said alkali metal or alkaline earth metal salt is added in a molar excess, relative to residual acidic halide in the alkoxy silane after said initial contacting with said alkali metal or alkaline earth metal alkoxide.

9. The method of claim 8 wherein said dissociation constant is between about $10^{-12}$ and $10^{-2}$.

10. The method of claim 8 wherein said dissociation constant is between about $10^{-9}$ and $10^{-4}$.

11. The method of claim 9 wherein said acid is selected from the group consisting of acetic acid, benzoic acid, propionic acid, phosphoric acid, sulfuric acid, sulfurious acid, formic acid, butyric acid, boric acid, succinic acid, glutaric acid, and adipic acid.

12. The method of claim 11 wherein said acid is acetic acid or propionic acid.

13. A method for reducing the quantity of acidic halide in an alkoxy silane comprising contacting said silane under substantially anhydrous conditions with a combination of an alkali metal or alkaline earth metal alkoxide and an alkali metal or alkaline earth metal salt of an acid, said acid having a dissociation constant ($K_a$) of greater than about $10^{-15}$, said combination having an amount of said alkoxide less than a molar equivalent amount relative to the quantity of said acidic halide in said alkoxy silane.

14. The method of claim 13 wherein said combination has a molar excess amount of said alkali metal or alkaline earth metal salt, when considering the amount of said alkoxide in combination therewith, relative to the quantity of said acidic halide in the alkoxy silane.

15. The method of claim 14 wherein said dissociation constant is between about $10^{-12}$ and $10^{-2}$.

16. The method of claim 14 wherein said dissociation constant is between about $10^{-9}$ and $10^{-4}$.

17. The method of claim 15 wherein said acid is selected from the group consisting of acetic acid, benzoic acid, propionic acid, phosphoric acid, sulfuric acid, sulfurious acid, formic acid, butyric acid, boric acid, succinic acid, glutaric acid, and adipic acid.

18. The method of claim 17 wherein said acid is acetic acid or propionic acid.

19. The method of claim 2, 3, 4, 5, 6, 8, 9, 10, 11, 12, 14, 15, 16, 17 or 18 wherein said alkoxy silane is an amino alkoxy silane.

20. The method of claim 2, 8 or 14 wherein said salt is sodium acetate or sodium propionate.

* * * * *